United States Patent [19]

Byers et al.

[11] Patent Number: 4,843,178

[45] Date of Patent: Jun. 27, 1989

[54] COMPOSITIONS POSSESSING PHEROMONE-LIKE ACTIVITY

[76] Inventors: Jim D. Byers, 1457 Oakdale Dr., Bartlesville, Okla. 74006; Charles A. Drake, Rte. 1, Box 206, Nowata, Okla. 74048

[21] Appl. No.: 127,864

[22] Filed: Dec. 2, 1987

[51] Int. Cl.$^4$ .................... C07C 45/29; C07C 45/30
[52] U.S. Cl. .................... 568/469.9; 568/470; 568/903; 568/471; 585/601; 585/616
[58] Field of Search ............... 568/469.9, 470, 471, 568/903; 560/261; 585/446, 647, 601, 616

[56] References Cited

U.S. PATENT DOCUMENTS

| | | | |
|---|---|---|---|
| 3,917,711 | 11/1975 | Roelofs et al. | 260/601 R |
| 4,083,995 | 4/1978 | Mitchell et al. | 424/311 |
| 4,219,542 | 8/1980 | Klun et al. | 424/84 |
| 4,269,780 | 5/1981 | Banasiak | 260/405 |
| 4,331,559 | 5/1982 | Banasiak | 252/429 R |
| 4,540,826 | 9/1985 | Banasiak et al. | 568/420 |
| 4,560,792 | 12/1985 | Banasiak | 560/261 |
| 4,609,498 | 9/1986 | Banasiak et al. | 260/410.9 R |
| 4,740,627 | 4/1988 | Byers et al. | 568/469.9 |

FOREIGN PATENT DOCUMENTS 0235742 2/1987 European Pat. Off. .

OTHER PUBLICATIONS

Tetrahedron Report, No. 34, vol. 33, "The Synthesis of Insect Sex Pheromones", by Clive A. Hendrick, pp. 1845, 1849–1851, and 1885.

*Insect Pheromones;* I. "Synthesis of Achiral Components of Insect Pheromones", by Renzo Rossi, pp. 820–821 (1977).

*Insect Suppression with Controlled Release Pheromone Systems,* vol. I and II; by Agis F. Kydonieus.

*Primary Examiner*—Werren B. Lone

[57] ABSTRACT

The present invention relates to a process for producing an E,Z-9-alkenyl-1-aldehyde component which comprises:

(a) disproportionating cyclooctene and an α-olefin in the presence of a suitable disproportionation catalyst under disproportionation conditions suitable to form a 1,9-alkadiene;

(b) reacting the 1,9-alkadiene obtained in step (a) with a suitable metallating agent under conditions suitable to form a 1-metallo-9-alkene;

(c) contacting the 1-metallo-9-alkene obtained in step (b) with oxygen under conditions suitable to form a 1-oxymetallo-9-alkene;

(d) hydrolyzing the 1-oxymetallo-9-alkene suit a suitable hydrolyzing agent, under suitable hydrolyzing conditions to form E,Z-9-alkenyl-1-alcohol.

(e) oxidizing said E,Z-9-alkenyl-1-alcohol with a suitable oxidizing agent under oxidizing conditions suitable to form E,Z-9-alkenyl-1-aldehyde. Another aspect of the invention pertains to a composition comprising Z-11-hexadecen-1-al, Z-9-tetradecen-1-al and E-9-tetradecen-1-al admixed in sufficient quantities to possess pheromone-like activity for *Heliothis zea* and *Heliothis virescens.*

20 Claims, No Drawings

COMPOSITIONS POSSESSING PHEROMONE-LIKE ACTIVITY

The present invention relates to a process which produces compositions which possess pheromone-like activity for the insects *Heliothis zea* and *Heliothis virescens*. Another aspect of the invention relates to a process for using said compositions to disrupt the mating of these insects. Still yet a further aspect pertains to a process for making 9-alkenyl aldehydes, such as E,Z-9-tetradecen-1-al.

BACKGROUND OF THE INVENTION

*Heliothis zea* is an insect which is more commonly known as the cottonboll worm, the corn ear worm, or the tomato fruit worm. This insect annually damages large quantities of corn, cotton and tomatoes.

*Heliothis virescens* is an insect which is more commonly known as the tobacco budworm. This insect also annually infests and damages large quantities of cotton as well as tobacco plants.

Due to environmental concerns about insecticides, individuals have explored alternative methods for eradicating these pests. One such method uses pheromones in order to disrupt the mating and subsequent reproduction of these insects.

Pheromone is the name given to a wide variety of organic compounds which fulfill a quasi-hormonal, or more accurately, an intraspecies communicational role. The female insect produces a minute amount of the pheromone which is detected by the male of the species and aids him in finding and mating with a female. Sex pheromones have enormous potential in insect control as they appear to be harmless to other forms of life and are relatively species specific. They may be used in a number of ways.

One such way is mating disruption. In mating disruption a sufficient quantity of the pheromone is distributed throughout a field so that the atmosphere is permeated with the pheromone. With the pheromone everywhere, the insect has great difficulty in locating a mating partner and therefore will be prevented from reproducing.

It is known that the mating of both *Heliothis zea* and *Heliothis virescens* can be disrupted by a 16:1 mixture of Z-11-hexadecen-1-al and Z-9-tetradecen-1-al.

Although this mixture is useful as a mating disruptant, known synthetic routes for its production are too cumbersome and expensive to be conducted economically in a large scale synthesis.

For example, U.S. Pat. No. 3,917,711 discloses a method for producing a admixture of Z-11-hexadecen-1-al and Z-9-tetradecen-1-al which comprises oxidizing a Z (cis) 9-tetradecenol into its corresponding aldehyde and Z (cis) 11-hexadecen-1-al from its corresponding alcohol. However, in such a process the starting materials must be isomerically pure. This can be accomplished by purchasing commercially available C-14 or C-16 alcohols and subjecting them to chromatography to separate the cis and trans isomers. However, this method is not amendable to being carried out economically on a large scale basis due to the stereochemical restraints.

Thus, it would be a valuable contribution to the art to develop compounds having pheromone-like activities for the pests *Heliothis zea* and *Heliothis virescens* that do not have to be isomerically pure, and can be economically produced.

OBJECT OF THE INVENTION

The object of the present invention to provide a novel process for synthesizing novel pheromone-like compounds.

It is a further object of the present invention to provide novel compositions possessing pheromone-like activity which contain a mixture of the trans and cis isomers.

It is yet another object of this invention to provide a process for utilizing these compositions in disrupting the mating of the pests *Heliothis zea* and *Heliothis virescens*.

In accordance with one embodiment of the present invention, we have discovered that an admixture of Z-11-hexadecen-1-al, Z-9-tetradecen-1-al and E-9-tetradecen-1-al can be used as a mating disruptant for the insects *Heliothis zea* and *Heliothis virescens*.

Other aspects, objects and advantages of the present invention will become apparent hereinafter from the following disclosure and appended claims.

DETAILED DESCRIPTION OF THE INVENTION

In this invention the Z and E-9-tetradecen-1-al isomers are conveniently synthesized by a process which comprises:

(a) disproportionating cyclooctene and 1-hexene in the presence of a suitable disproportionation catalyst under disproportionation conditions suitable to form 1,9-tetradecadiene;

(b) reacting the 1,9-tetradecadiene obtained in step (a) with a suitable metallating agent under conditions suitable to form a 1-metallo-9-tetradecene;

(c) contacting the 1-metallo-9-tetradecene obtained in step (b) with oxygen under conditions suitable to form a 1-oxymetallo-9-tetradecene;

(d) hydrolysing the 1-oxymetallo-9-tetradecene with a suitable hydrolysing agent, under suitable hydrolysing conditions to form E,Z-9-tetradecen-1-ol; and (e) oxidizing said E,Z-9-tetradecen-1-ol with a suitable oxidizing agent under oxidizing conditions suitable to form E,Z-9-tetradecen-1-al.

The process outlined above is suitable for producing 9-alkenyl-1-aldehydes other than E,Z-9-tetradecen-1-al. 9-alkenyl-1-aldehydes which can be produced by the process of the present invention can be represented by the formula,

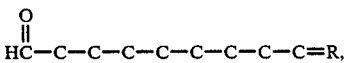

wherein R is selected from the group consisting of those alkyl groups containing from 2 to 11 carbon atoms.

The starting materials for producing a 9-alkenyl-1-aldehyde in accordance with this embodiment of the present invention is cyclooctene and an alpha-olefin having 3 to 12 carbon atoms. Since all of the carbon atoms of both the cyclooctene and the alpha-olefin will be retained in the final product, the appropriate alpha-olefin is selected so as to define the total chain length of the desired 9-alkenyl-1-aldehyde.

For E,Z-9-tetradecen-1-al, the appropriate alpha-olefin would be 1-hexene.

The disproportionation of cyclooctene and the alpha-olefin can be carried out in a variety of ways as recognized by those of skill in the art. Thus, any suitable ratio of cyclooctene/alpha-olefin can be employed in the presence of a wide variety of disproportionation catalysts. For the most efficient utilization of the olefinic reactants, a molar ratio of about 1:1 is preferred, although good conversions are obtained with cyclooctene/alpha-olefin ratios ranging from about 5:1 to about 1:5.

A wide variety of heterogeneous and homogeneous disproportionation catalysts are known in the art and are capable of promoting the disproportionation of cyclooctene and an alpha-olefin to produce a 1,9-alkadiene. Our invention is not limited to the use of a specific disproportionation catalyst.

Suitable catalysts for use in the disproportionation reaction of the present invention include:

(1) silica or thoria promoted by an oxide or compound convertible to an oxide by calcination, or sulfide of tungsten or molybdenum; or by an oxide or compound convertible to an oxide by calcination of rhenium or tellurium;

(2) alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;

(3) one or more of the group aluminum phosphate, zirconium phosphate, calcium phosphate, magnesium phosphate, or titanium phosphate promoted by one or more of a sulfide of molybdenum or tungsten, or an oxide or compound convertible to an oxide by calcination of molybdenum, tungsten or rhenium or magnesium tungstate or beryllium phosphotungstate;

(4) silica, alumina, aluminum phosphate, zirconium phosphate, calcium phosphate, magnesium phosphate, or titanium phosphate promoted by a hexacarbonyl of molybdenum or tungsten; and (5) (a) molybdenum oxide or tungsten oxide associated with suitable support material and (b) at least one organoaluminum compound, optionally, treated with nitric oxide or nitrosyl halides.

These catalysts as well as their methods of activation are known in the art. The conditions under which a disproportionation reaction would be carried out with these catalysts is also known in the art. U.S. Pat. No. 4,609,498 issued to Banasiak et al which is currently assigned to Phillips Petroleum Company, discloses these catalysts, their methods of preparation, and suitable reaction conditions for carrying out disproportionation reactions with these catalysts. This reference is hereby incorporated by reference.

The presently preferred disproportionation catalyst is a silica-supported molybdenum catalyst.

The anion associated with the molybdenum is not critical, but is preferably an oxide or sulfide. The catalyst can be activated by heating it in an inert atmosphere.

If desired, the molybdenum can be washed with a base such as potassium hydroxide, sodium hydroxide, or ammonium hydroxide prior to or after it has been contacted with the silica.

The manner in which the disproportionation reaction is carried out is not critical to the practice of the present invention. Generally, the alpha-olefin and the cyclooctene will be contacted with a silica-supported molybdenum catalyst in the presence of heat.

Generally, the disproportionation reaction should be carried out at a temperature range of from 40° C. to 300° C., and more preferably from 120° C. to 220° C. The pressure in the reaction environment should generally be in the broad range of 50 to 1500 psig and more preferably from 100 to 400 psig.

If the reaction is conducted in a batch wise manner, then it is preferred that the reaction be carried out for a period of time ranging from 0.5 hours to 18 hours.

If the reaction is carried out in a continuous reactor, then it is preferred that the reaction have a weight hour velocity of 0.5 to 70 grams/grams/hour, more preferably from 1 to 40 grams/grams/hour.

The next step in the synthesis of the Z and E-9-alkenyl-1-aldehyde is to metallate the 1,9-alkadiene obtained in the disproportionation reaction of step (a) in order to form a 1-metallo-9-alkene.

The metallation of the 1,9-alkadiene to form a 1-metallo-9-alkene can be carried out employing a variety of metallating agents. Any metallating agent capable of selective reaction with the terminal double bond of the diene starting material is suitable. Examples of suitable metallating agents include organoboranes, organoaluminum compounds, organomagnesium compounds, and the like. Organoaluminum compounds are currently preferred.

Organoboranes contemplated to be within the scope of the present invention can be described as "hindered" organoborane compounds and can be represented by the following formula:

$$R_2BH$$

wherein each R is independently selected from the group consisting of $C_2$ to $C_{10}$ hydrocarbon radicals, wherein at least one R group is a secondary or tertiary alkyl group and each R group can be connected to the other as part of a ring structure. Exemplary compounds which satisfy the above formula include disiamylborane (i.e., bis-(3-methyl-2-butyl)borane), 9-boradicyclo[3.3.1-]nonane (9-BBN), dithexylborane, thexylcyclopentylborane, thexylcyclohexylborane, and the like.

The hydroboration reaction is generally carried out in the presence of a suitable solvent such as, for example, tetrahydrofuran (THF). Preferably, a roughly equimolar mixture of diene and organoborane reagent are combined. Suitable molar ratios of organoborane to 1,9 alkadiene range from 0.5:1 to 2:1. Typically, the hydroboration reaction should be carried out in an inert atmosphere; i.e. moisture and oxygen should be excluded from the reaction mixture. Reaction conditions employed are broadly 0°-100° C. for a few minutes up to several hours. Preferably, the hydroboration is carried out at about 20°-80° C. for 15 minutes up to about 2 hours. Reaction is generally carried out at about atmospheric pressure, although higher and lower pressures are acceptable.

Organomagnesium compounds contemplated to be within the scope of the present invention can be described by reference to the following formulae:

$$R'MgX, \text{ and}$$

$$R'_2Mg$$

wherein R' is selected from the group consisting of a $C_3$ to $C_{10}$ hydrocarbon radical, more preferably a $C_3$ to $C_6$ hydrocarbon radical; which has at least one $\beta$-hydrogen and X is selected from the group consisting of Cl, Br or I. Exemplary compounds which satisfy the above formulae include various Grignard reagents, such as, for example, butylmagnesium bromide, isopropylmagnesium bromide, and the like. Additional examples include dialkyl magnesium compounds such as for example diethylmagnesium, diisopropylmagnesium and the like.

Metallation with organomagnesium compounds is generally carried out in the presence of at least one transition metal activating agent. Suitable transition metal activating agents include nickel, titanium, vanadium and zirconium compounds. Exemplary titanium activating agents include a titanocene dichloride such as, for example, dicyclopentadiene titanium dichloride or alternatively, titanium tetrachloride.

The molar ratio of organomagnesium compound to diene should be at least about 1:1 with the presence of an excess of the organomagnesium compound acceptable, i.e., up to about a 5 to 1 molar ratio. The molar ratio of diene to transition metal reagent is generally in the range of about 1–500:1 and preferably about 50–100:1.

Metallation with organomagnesium compounds is generally carried out at atmospheric pressure, although higher and lower pressures are operable. Preferably, atmospheric pressure or slightly reduced pressures will be employed since pressures in excess of atmospheric will tend to retard the reaction rate. Reaction temperatures of about 20° to about 100° C. for at least one minute up to about 24 hours are suitable. Preferably, reaction temperature will be maintained between about 20° and 60° C. for about 15 minutes to about 6 hours.

Organoaluminum compounds contemplated to be within the scope of the present invention can be described by reference to the formula $R_2AlH$, wherein each R is independently selected from the group consisting of $C_2$ to $C_{10}$ hydrocarbon radicals, wherein at least one R group is a secondary or tertiary alkyl group and each R group can be connected to the other as part of a ring structure. Examples of suitable organoaluminum compounds can be selected from the group consisting of diisobutyl aluminum hydride, diisopropyl aluminum hydride, dimethyl aluminum hydride and aluminum hydride.

Metallation with organoaluminum compounds is generally carried out at atmospheric pressure, although higher and lower pressures are operable. Preferably atmospheric pressure or slightly reduced pressures will be employed since pressures in excess of atmospheric tend to retard the reaction rate. Reaction temperatures of about 20° to about 100° C. for at least one minute up to about 24 hours are suitable. Preferably, the reaction temperature will be maintained between about 20° and 60° C. for about 15 minutes to about 6 hours.

It is preferred for the 1,9-alkadiene to be present in a slight molar excess relative to the organoaluminum compound, suitable molar ratios of organoaluminum compound to 1,9-alkadiene will be within the range of from 0.1:1 to 2:1.

The next step in the synthesis of the E and Z-9-alkenyl-1-aldehyde is to contact the 1-metallo-9-alkene obtained in step (b) with oxygen under conditions suitable to form a 1-oxymetallo-9-alkene.

Any suitable source of oxygen can be employed, such as for example, air, oxygen-enriched air, pure oxygen, etc. The flow rate of oxygen introduced into the reaction mixture containing the 1-metallo-9-alkene will be varied as required to maintain the desired reaction temperature during the oxidation step.

Generally, a reaction temperature within the range of room temperature to about 100° C. is employed, with a temperature in the range of about 25° to 60° C. being preferred.

Optionally, various metal compound promoters, such as, for example, copper, zinc, and the like can be added during the oxidation step to aid in carrying the reaction to completion.

The next step in the synthesis of the Z and E 9-alkenyl-1-aldehyde is to hydrolyze the 1-oxymetallo-9-alkene obtained in step (c) with a suitable hydrolysing agent under suitable hydrolysing conditions to form an E,Z-9-alkenyl-1-alcohol.

This hydrolysis of the 1-oxymetallo function into the corresponding alcohol can be accomplished by contacting the 1-oxymetallo 9-alkene with a suitable hydrolysing agent.

Representative examples of suitable hydrolysing agents can be selected from the group consisting of hydrochloric acid, sulfuric acid, phosphoric acid, and acetic acid. It is currently preferred that the acid utilized have a molarity in the range of 1 molar to 3 molar.

It is presently preferred that the contact between the 1-oxymetallo-9-alkene and the hydrolysing agent be conducted at a temperature in the range of from 25° to 40° C.

It is also currently preferred that the 1-oxymetallo-9-alkene be contacted with the hydrolysing agent for a period of time ranging from 15 minutes to 45 minutes.

Generally, it is preferred that there be a slight excess of hydrolyzing agent present relative to the 1-oxymetallo-9-alkene. However, suitable molar ratios of 1-oxymetallo-9-alkene to hydrolysing agent range from 1:1 to 1:5.

The final step in the synthesis of the E,Z-9-alkenyl-1-aldehyde is to oxidize the E,Z-9-alkenyl-1-alcohol obtained in step (d) with a suitable oxidizing agent under suitable oxidizing conditions into a Z,E-9-alkenyl-1-aldehyde.

One group of suitable oxidizing agents are those selected from the group consisting of pyridinium chlorochromate and pyridinium dichromate. Another suitable oxidizing agent is DMSO (dimethyl sulfoxide).

If the oxidation is conducted with either pyridinium chlorochromate or pyridinium dichromate, then it is preferred that the oxidizing agent be present in a molar excess relative to the E,Z-9-alkenyl-1-alcohol. Suitable ratios of oxidizing agents to E,Z-9-alkenyl-1-alcohol will be in the range of from 1:1 to 5:1, more preferably 1.5:1 to 3:1.

Typical reaction conditions with the pyridinium oxidizing agents will include a reaction temperature in the range of from 20° C. to 50° C., for a period of time ranging from 15 minutes to 3 hours.

It is also preferred that the reaction be conducted in an organic halide solvent, such as methylene chloride.

The E,Z-9-alkenyl-1-aldehyde can be separated from the reaction medium by an extraction step utilizing an oxygenated organic solvent such as an ether.

The E,Z-9-alkenyl-1-aldehyde can then be separated from the oxygenated organic phase by wiped film distillation at a temperature of 160° C. to 167° C. and at a pressure of 0.2 mm Hg.

If DMSO is utilized as the oxidizing agent, then it is preferred that the oxidation be conducted in the presence of an activator; suitable activators can be selected from the group consisting of oxalyl chloride, trifluroacetic anhydride, acetic anhydride, and thionyl chloride.

It is also preferred that the activator be present in a molar excess relative to the E,Z-9-alkenyl-1-alcohol. Suitable ratios of activator to E,Z-9-alkenyl-1-alcohol will be in the range of from 1:1 to 5:1, more preferably 1.5:1 to 3:1.

It is also preferred that the oxidation with DMSO be conducted in the presence of an organic amine base. Suitable organic amine bases can be selected from the group consisting of those organic amine bases represented by the formula,

wherein each R group is independently selected from the group consisting of hydrogen or a $C_1$–$C_{10}$ hydrocarbon radical, with the limitation that at least one R group is a hydrocarbon radical. Another suitable organic amine is pyridine.

It is currently preferred that the oxidizing agent, DMSO, be present in the reaction zone in a molar excess relative to the E,Z-9-alkenyl-1-alcohol. Suitable ratios of DMSO to the E,Z-9-alkenyl-1-alcohol will be in the range of from 1:1 to 5:1, more preferably 1.5:1 to 3:1.

It is also preferred that the organic amine base be present in the reaction zone in a molar excess relative to the E,Z-9-alkenyl-1-alcohol. Suitable ratios of organic amine base to E,Z-9-alkenyl-1-alcohol will be in the range of from 1:1 to 5:1, more preferably 1.5:1 to 3:1.

Typically, the reaction will be conducted at a temperature range of from −60° C. to 0° C. for a period of time ranging from 15 minutes to 6 hours.

It is also preferred that the reaction be conducted in an organic solvent, such as ether, methylene chloride or tetrahydrofuran.

The E,Z-9-alkenyl-1-aldehydes can be separated from the reaction zone by adding water to the reaction zone and extracting the E,Z-9-alkenyl-1-aldehyde. The by-products will be concentrated in the water phase and the E,Z-11-tetradecen-1-al will be concentrated in the organic phase.

The E,Z-9-alkenyl-1-aldehyde can then be separated from the organic phase by wiped film distillation at a temperature of 160° C. to 167° C. and at a pressure of 0.2 mm Hg.

E,Z-9-alkenyl-1-aldehyde may then be admixed with Z-11-hexadecen-1-al which will function as a mating disruptant for the insect *Heliothis zea* and *Heliothis virescens*.

It is presently preferred for the Z-11-hexadecen-1-al to be present in the composition in the quantity of from about 94 to 98 mole percent, for the Z-9-tetradecen-1-al to be present in the quantity of from about 2 to 5.9 mole percent, and for the E-9-tetradecen-1-al to be present in the quantity of from about 0.1 to 4 mole percent. The most preferred composition of the present invention contains about 94 mole percent of the Z-11-hexadecen-1-al, about 3 mole percent of the Z-9-tetradecen-1-al and about 3 mole percent of the E-9-tetradecen-1-al.

The exact manner in which the Z-11-hexadecen-1-al, Z-9-tetradecen-1-al and E-9-tetradecen-1-al are mixed is not critical to the practice of the present invention. These compounds can be mixed in any method conventionally used within the industry.

The exact manner in which this pheromone-like composition is applied to the fields in order to disrupt the mating of the *Heliothis zea* and *Heliothis virescens* is not critical to the practice of the present invention. Typically, the composition will be incorporated into a polymer matrix capable of slowly releasing the pheromone-like composition into the atmosphere.

Suitable polymer matrixes as well as methods of impregnating pheromone or pheromone-like compounds into these polymer matrixes are known in the art. For example, *Insect suppression with controlled release pheromone systems* by Kydonieus et al, CRC Press Inc., (1982), discloses suitable methods for producing controlled release pheromone systems.

The manner in which these controlled release pheromone systems are distributed through the field is also not critical to the practice of the present invention. They can be distributed by air, hand, or any other method typically used in the industry.

The manner in which the Z-11-hexadecen-1-al utilized in the present invention is synthesized is not critical to the practice of the present invention. Z-11-hexadecen-1-al is available from numerous commercial suppliers and any of the commercially available materials are suitable for use in the present invention.

The manner in which the E and Z-9-tetradecen-1-al is synthesized, is also not critical to the practice of the present invention. Both Z and E isomers of 9-tetradecen-1-al are available commercially. Any of the commercially available compounds are suitable for use in the present invention.

A further understanding of the present invention and its advantages will be provided by reference to the following examples.

Example I

The purpose of this example is to demonstrate a method for carrying out the disproportionation reaction between cyclooctene and the alpha-olefin 1-hexene, thereby forming 1,9-tetradecadiene.

A. Disproportionation Catalyst Preparation

Various disproportionation catalysts were prepared by pouring an aqueous solution of the catalyst precursor over a quantity of catalyst support contained in a beaker fastened to a rotating table. The solution was added at a rate that permitted good absorption of the solution on the silica support.

Catalyst 1 was prepared by pouring 26 ml of a solution containing 3 grams of ammonium molybdate over 20 gm of a high surface area silica support. Once all the support treating solution had been added to the support, the treated support was dried in an oven at a temperature of 120° C. and then calcined at 450° C.

Catalyst 2 was prepared by pouring 26 ml of a solution containing 2.6 gm of ammonium molybdate and 0.05 gm potassium hydroxide over 20 gm of a high surface area silica support. Once all the support treating solution had been added to the support, the treated support was oven dried at 120° C. for one hour, after which the temperature was increased to 350° C. for an additional 3 hours.

Catalyst 3 was prepared by pouring 50 ml of a solution containing 5 gm of ammonium molybdate over 40 gm of a high surface area silica support. Once all the support treating solution had been added to the support, the treated support was oven dried at 120° C. for approximately 1 to 2 hours and then calcined at 350° C. for an additional 3 hours.

Catalyst 4 was prepared by pouring 26 ml of a solution containing 3.2 gm of a molybdate and 0.05 gm of potassium hydroxide over 20 gm of a high surface area silica support. Once all the support treating solution had been added to the support, the treated support was oven dried at a temperature of 120° C. and the calcined at a temperature of 350° C. for about 3 hours.

Catalyst 5 was prepared by pouring 45 ml of a solution containing 1.9 gm of ammonium molybdate over 20 gm of a high surface area alumina support. Once all the support treating solution had been added to the support, the treated support was oven dried at 450° C. for about 3 hours.

Catalyst 6 was prepared by pouring 11 ml of a solution containing 0.8 gm of ammonium tungstate and 0.1 gm of potassium hydroxide over 10 gm of high surface area silica support. Once all the support treating solution had been added to the support, the treated support was oven dried at 350° C. for about 3 hours.

Catalyst 7 was prepared by pouring 26 ml of a solution containing 1.6 gm of ammonium tungstate and 0.05 gm potassium hydroxide over 20 gm of high surface area silica support. Once all the support treating solution had been added to the support, the treated support was oven dried at 120° C. for one hour and at 350° C. for an additional 3 hours.

2.5 or 5 gm of each of the above-described catalysts was then loaded into a vertical pipe reactor (½ inch diameter by about 20 inches in length). The catalysts were then air oxidized for about 6 hours at 450° C., then CO treated at 450° C. and 125 psig for about 1 hour and finally cooled to the desired reaction temperature.

B. Disproportionation Reaction

Various quantities of cyclooctene and 1-hexene were passed through a guard bed of about ⅓ 3A molecular sieves, ⅓-13X molecular sieves and ⅓ gamma alumina. The pretreated feed was then introduced at the rate of about 1 to 4 mls. per minute to the catalyst bed prepared as described above which was maintained at a reaction temperature ranging from 135° C. to 350° C. and at a reaction pressure ranging from 100 to 200 lbs.

The following results were obtained.

invention that makes it suitable for economical large scale industrial synthesis.

EXAMPLE II

The purpose of this example is to demonstrate a preferred manner of preparing E,Z 9-tetradecen-1-ol by:

(a) converting 1,9 tetradecadiene into 1-metallo-9-tetradecene;

(b) converting the 1-metallo-9-tetradecene obtained in step (a) into 1-oxymetallo-9-tetradecene; and (c) hydrolysing the 1-oxymetallo-9-tetradecene into E,Z-9-tetradecen-1-ol.

A 0.5 liter, 3-necked flask equipped with a mechanical stirrer, addition funnel and reflux condenser was charged with 50 grams (0.2573 moles) of 1,9-tetradecadiene.

The diisobutyl aluminum hydride in heptane, 18.2 mls. (14.525 grams, 0.1022 moles) was added to the addition funnel and added dropwise to the diene over about a half hour; the mixture was then heated to 110° C. and maintained at that temperature for about 2 hours.

After the diene and aluminum compounds had been heated, the reaction mixture was cooled to room temperature, and oxygen bubbled into the reaction mixture. After oxygen bubbling had proceeded for about a half hour, 0.0975 grams of cupric chloride was added, and oxygen introduction continued for another 3 hours.

The product was hydrolysed by adding about 0.5 liters of about a 4 molar HCl solution to the organic reaction mixture. The layers were then separated and the organic layer was washed with 2 liters of a saturated sodium bicarbonate solution. The organic layer was separated, dried and then concentrated on a rotary evaporator at reduced pressure.

The E,Z-9-tetradecen-1-ol was recovered by distillation at a temperature of 145 to 147 and at a pressure of 0.02 mm. Hg. The yield of E,Z-9-tetradecen-1-ol was 75 percent based on the amount of starting diene as determined by distillation.

It is important to point out that 3 *different* synthetic steps occurred during the reaction sequence set out in this example. Heating the 1,9-tetradecadiene in the presence of the diisobutyl aluminum hydride produced a

TABLE I

| Run # | Catalyst # | Quant. Catalyst | Quant. Cyclooctene | Quant. Hexene | Rx Temp. | Rx Press | Feed Rate ml./min. | Yield 1,9-tetra-decatriene (wt %) |
|---|---|---|---|---|---|---|---|---|
| 1 | 1 | 5 gm. | 330 gm. | 672 gm. | 135° C. | 100 lbs. | 1 | 4.78 |
| 2 | 2 | 5 gm. | 330 gm. | 672 gm. | 135° C. | 100 lbs. | 1 | 8.68 |
| 3 | 6 | 5 gm. | 825 gm. | 1680 gm. | 350° C. | 200 lbs. | 3 | 1.83 |
| 4 | 2 | 5 gm. | 660 gm. | 1344 gm. | 140° C. | 200 lbs. | 4 | 5.41 |
| 5 | 6 | 2.5 gm. | 660 gm. | 1344 gm. | 350° C. | 200 lbs. | 4 | 3.25 |
| 6 | 2 | 5 gm. | 660 gm. | 1344 gm. | 140° C. | 200 lbs. | 4 | 4.11 |
| 7 | 3 | 5 gm. | 660 gm. | 1344 gm. | 140° C. | 200 lbs. | 4 | 5.42 |
| 8 | 4 | 5 gm. | 660 gm. | 1344 gm. | 140–180° C. | 200 lbs. | 4 | 5.84 |
| 9 | 7 | 2.5 gm. | 660 gm. | 1344 gm. | 200° C. | 200 lbs. | 4 | 1.04 |
| 10 | 4 | 5 gm. | 660 gm. | 1344 gm. | 140° C. | 200 lbs. | 4 | 1.64 |
| 11 | 5 | 5 gm. | 660 gm. | 1344 gm. | 140° C. | 200 lbs. | 2–4 | 1.94 |

These experimental runs demonstrate that the disproportionation reaction of the present invention can be utilized with numerous catalysts under a variety of conditions. The yield of 1,9-tetradecadiene varied from about 1 to about 9 weight percent as calculated by gas-liquid chromatographic analysis.

Approximately 60–90 percent of the reaction product was unreacted 1-hexene and unreacted cyclooctene. These unreacted reagents can be recycled and utilized in subsequent reactions. This ability to recycle unreacted reagents is one of the advantages of the present 1-metallo-9-dodecene. This 1-metallo-9-dodecene was then transformed into a 1-oxymetallo-9-dodecene by contacting the metallo compound with cuprous chloride in the presence of oxygen. Finally, the 1-oxymetallo-9-dodecene was hydrolyzed into E,Z-9-tetradecen-1-ol by contacting the oxymetallo compound with hydrochloric acid.

Thus, in addition to a high yield, the present invention also has the advantage of not requiring a separation and recovery after every step in the synthesis.

EXAMPLE III

The purpose of this example is to demonstrate one of the several methods which are suitable ior oxidizing an E,Z-9-alkenyl-1-alcohol into an E,Z-9-alkenyl-1-aldehyde.

28 Grams (0.13 moles) of E,Z-9-tetradecen-1-ol had been prepared in the manner disclosed in Example I and Example II.

A 2 liter, 3-necked flask equipped with a mechanical stirrer, addition funnel, and reflux condenser was charged with 42.6 grams (0.20 moles) of pyridinium chlorochromate and 500 mls of methylene chloride. The 28 grams of E,Z-9-tetradecen-1-ol and an additional 100 mls of methylene chloride were placed in the addition funnel of the 3-necked flask.

The E,Z-9-tetradecen-1-ol was dripped into the reaction zone over about a 20 minute period.

The reaction mixture was then stirred for about 1 hour at room temperature. The E,Z-9-tetradecen-1-al was recovered from the reaction mixture in the following manner.

The reaction mixture was washed three times with about 250 mls of ether. After each washing, the liquid was decanted off and saved.

The decanted liquid was then collected together and concentrated on a rotary evaporator. After concentration, the liquid was then wiped-film distilled at a surface temperature of about 167° C. and about 0.2 mm of mercury.

The yield of E,Z 9-tetradecen-1-al was about 85 percent based upon the distillation yield.

Thus, the above example demonstrates that pyridinium chlorochromate will oxidize the E,Z 9-tetradecen-1-ol into E,Z 9-tetradecen-1-al in yields high enough to be conducted economically on a large scale industrial synthesis.

EXAMPLE IV

The purpose of this example is to demonstrate that the oxidizing agent, DMSO, will also oxidize E,Z 9-tetradecen-1-ol into E,Z 9-tetradecen-1-al at yields high enough to support an economically viable large scale industrial synthesis.

21.2 Grams (0.0998 moles) of E,Z 9-tetradecen-1-ol was prepared in the manner described in Example I and Example II.

A 1000 ml 3-necked flask equipped with a mechanical stirrer, addition funnel and reflux condenser was charged with 0.2293 moles of oxalyl chloride, and 250 mls of ethyl acetate. The flask was then cooled to $-15°$ C.

The addition funnel of the flask was charged with 0.4791 moles of DMSO and 50 mls of ethyl acetate. DMSO and ethyl acetate were then dripped into the reaction mixture over about a 10 minute period while maintaining the reaction mixture at a temperature of about $-15°$ C.

The addition funnel was then charged with 21.2 grams of E,Z-9-tetradecen-1-ol and 25 mls of ethyl acetate. The E,Z-9-tetradecen-1-ol and the ethyl acetate were then dripped in over a 5 minute period, while maintaining the reaction mixture at a temperature of about $-15°$ C.

The reaction mixture was then stirred for 15 minutes and 0.5022 moles of triethyl amine were added to the reaction mixture.

The reaction mixture was stirred for an additional 5 minutes at $-15°$ C.

At that point, the reaction mixture was allowed to warm to room temperature and the E,Z-9-tetradecen-1-al was recovered.

The E,Z-9-tetradecen-1-al was recovered in the following method: 200 mls of $H_2O$ and 200 mls of ethyl acetate were added to the reaction mixture. The E,Z-9-tetradecen-1-al was concentrated in the organic phase. These phases were separated and the organic phase was concentrated on a rotary evaporator.

After concentration, the E,Z-9-tetradecen-1-al was recovered by wiped-film distillation conducted at a surface temperature of about 150° C. and about 0.2 mm of Hg.

The yield of E,Z-9-tetradecen-1-al was 95 percent based upon the distilled yield.

Thus, this example demonstrates that when DMSO is utilized as an oxidizing agent, E,Z-9-alkenyl-1-alcohols such as E,Z-9-tetradecen-1-ol can be converted into E,Z-9-alkenyl-1-aldehydes at yields high enough to permit the large scale industrial synthesis of the desired pheromone.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of the patent protection desired and sought.

That which is claimed is:

1. A process for producing E,Z-9-alkenyl-1-aldehydes comprising:
   (a) disproportionating cyclooctene and an alpha-olefin containing from 3 to 12 carbon atoms in the presence of a disproportionation catalyst selected from the group consisting of
      (1) silica or thoria promoted by an oxide or compound convertible to an oxide by calcination, or sulfide of tungsten or molybdenum; or by an oxide or compound convertible to an oxide by calcination of rhenium or tellurium;
      (2) alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;
      (3) one or more of the group aluminum phosphate, zirconium phosphate, calcium phosphate, magnesium phosphate, or titanium phosphate promoted by one or more of a sulfide of molybdenum or tungsten, or an oxide or compound convertible to an oxide by calcination of molybdenum, tungsten or rhenium or magnesium tungstate or beryllium phosphotungstate;
      (4) silica, alumina, aluminum phosphate, zirconium phosphate, calcium phosphate, magnesium phosphate, or titanium phosphate promoted by a hexacarbonyl of molybdenum or tungsten; and
      (5) (a) molybdenum oxide or tungsten oxide associated with suitable support material and (b) at least one organoaluminum compound, optionally, treated with nitric oxide or nitrosyl halides, selected from the group consisting of organoaluminum compounds which have the formula $R''_a AlX_b$ where $R''$ is a saturated aliphatic or aromatic hydrocarbon having up to about 20 carbon atoms. X is chlorine, bromine, iodine, or fluorine, a is an integer of at least 1, b can be 0, 1 or 2, and the total of a and b is 3, thus a can be 1, 2 or 3 producing a 1,9-alkadiene;

(b) reacting the 1,9-alkadiene obtained in step (a) with a metallating agent selected from the group consisting of:

(1) organoboranes of the formula $R_2BH$ wherein each R is independently selected form the group consisting of $C_2$ to $C_{10}$ hydrocarbon radicals, wherein at least one R group is a secondary or tertiary alkyl group and each R group can be connected to the other as part of a ring structure;

(2) organomagnesium compounds of the formulae R'MgX or $R_2Mg$ wherein each R is independently selected from the group consisting of a $C_3$–$C_{10}$ hydrocarbon radical having at least one β hydrogen and X is selected from the group consisting of Cl, Br, or I; and (3) organoaluminum compounds selected from the group consisting of $AlH_3$ and compounds of the formula $R_2AlH$ wherein each R group is independently selected from the group consisting of $C_1$ to $C_{10}$ hydrocarbon radicals, wherein at least one R group is a secondary or tertiary alkyl group and each R group can be connected to the other as part of a ring structure producing a 1-metallo-9-alkene;

(c) contacting the 1-metallo-9-alkene obtained in step (b) with oxygen, producing a 1-oxymetallo-9-alkene;

(d) hydrolysing the 1-oxymetallo-9-alkene obtained in step (c) with a hydrolysing agent selected from the group consisting of hydrochloric acid, sulfuric acid, phosphoric acid and acetic acid, producing an E,Z-9-alkenyl-1-alcohol;

(e) oxidizing the E,Z-9-alkenyl-1-alcohol obtained in step (d) with an oxidizing agent selected from the group consisting of pyridinium chlorochromate, pyridinium dichromate and, dimethyl sulfoxide, producing an E,Z-9-alkenyl-1-aldehyde.

2. The process of claim 1, wherein
(a) the molar ratio of said cyclooctene to said alpha-olefin is within the range of from 5:1 to 1:5;
(b) wherein the molar ratio of said metallating agent to said 1,9-alkadiene is within the range of:
(1) 0.5:1 to 2:1 when said metallating agent is an organoborane;
(2) 1:1 to 5:1 when said metallating agent is an organomagnesium compound; and
(3) 0.1:1 to 2:1 when said metallating agent is an organoaluminum compound.
(c) the molar ratio of said 1-oxymetallo-9-alkene to said hydrolysing agent is within the range of from 1:1 to 1:5; and
(d) the molar ratio of said oxidizing agent to said E,Z-9-alkenyl-1-alcohol is within the range of from 1:1 to 5:1.

3. The process of claim 1 wherein said 1-metallo-9-alkene is contacted with oxygen in the presence of a metal promoter selected from the group consisting of copper and zinc.

4. The process of claim 1 wherein said oxidation is conducted with dimethyl sulfoxide.

5. The process of claim 4 wherein said oxidation with said dimethyl sulfoxide is conducted in the presence of an activator selected from the group consisting of oxalyl chloride, trifluroacetic anhydride, acetic anhydride, and thionyl chloride.

6. The process of claim 5 wherein the molar ratio of said activator to said dimethyl sulfoxide is in the range of from 1:1 to 5:1.

7. The process of claim 5, wherein the molar ratio of said activator to said E,Z-9-alkenyl-1-alcohol is within the range of from 1:1 to 5:1.

8. The process of claim 5 wherein said oxidation with said dimethyl sulfoxide is conducted in the presence of an organic amine base selected from the group consisting of those organic amine bases represented by the formula $$\overset{R}{\underset{|}{RNR}}$$

wherein each R group is independently selected from the group consisting of hydrogen or hydrocarbon radicals containing from 1 to 10 carbon atoms, with the limitation that at least one R group be a hydrocarbon radical and pyridine.

9. The process of claim 8, wherein said oxidation is conducted in the presence of an organic amine base selected from the group consisting of triethylamine, trimethylamine, tripropylamine, tributylamine, tripentylamine, trihexylamine, and pyridine.

10. The process of claim 9, wherein the molar ratio of said organic amine base to said dimethylsulfoxide is in the range of from 1:1 to 5:1.

11. The process of claim 8, wherein the molar ratio of said organic amine base to said E,Z 9-alkenyl-1-alcohol is within the range of from 1:1 to 5:1.

12. The process of claim 1 wherein said oxidation agent is pyridinium dichromate.

13. The process of claim 12 wherein said oxidation is conducted at a temperature range of from 20° C. to 50° C.

14. The process of claim 3, wherein
(a) said alpha-olefin is 1-hexene;
(b) said disproportionation catalyst is molybdenum oxide on a silica support;
(c) said metallating agent is diisobutyl aluminum hydride;
(d) said metal promoter is cupric chloride;
(e) said hydrolysing agent is hydrochloric acid; and
(f) said oxidizing agent is pyridinium chlorochromate.

15. The process of claim 8, wherein
(a) said alpha-olefin is 1-hexene;
(b) said disproportionation catalyst is molybdenum oxide on a silica support;
(c) said metallating agent is diisobutyl aluminum hydride;
(d) said contact between said oxygen and a 1-aluminum-9-tetradecene is conducted in the presence of cupric chloride;
(e) said hydrolysing agent is hydrochloric acid; and
(f) said oxidation is conducted in the presence of oxalyl chloride and triethylamine.

16. The process of claim 15, wherein said contact with oxygen is conducted at a temperature range of from 20° C. to 100° C.

17. A pheromone composition which comprises
(a) E-9-tetradecen-1-al
(b) Z-9-etradecen-1-al
(c) Z-11-hexadecen-1-al wherein a and b are produced by the process of claim 1 and E-9-tetradecenal, Z-9-tetradecen-1-al and Z-11-hexadecen-1-al are present in an amount sufficient to render the composition disruptive of the mating of *Heliothis zea* and *Heliothis virescens*.

18. The composition of claim 17 wherein;
(a) said Z-11-hexadecen-1-al is present in the quantity of from about 94–98 mole percent;
(b) said Z-9-tetradecen-1-al is present in the quantity of from about 2 to 5.9 mole percent; and
(c) said E-9-tetradecen-1-al is present in the quantity of from about 0.1 to 4 mole percent.

19. The composition of claim 1, wherein
(a) said Z-11-hexadecen-1-al is present in the quantity of about 94 mole percent;
(b) said Z-9-tetradecen-1-al is present in the quantity of about 3 mole percent; and
(c) said E-9-tetradecen-1-al is present in the quantity of about 3 mole percent.

20. A process for disrupting the mating of the insects *Heliothis zea* and *Heliothis virescens* using the composition of claim 17 comprising:
introducing into an environment containing said insects, a composition further comprising Z-11-hexadecen-1-al present in the quantity of about 94 to 98 mole percent, Z-9-tetradecen-1-al present in the quantity of about 2 to 5.9 mole percent, and E-9-tetradecen-1-al present in the quantity of about 0.1 to 4 mole percent.

* * * * *